United States Patent [19]
Kruzel et al.

[11] Patent Number: 5,925,318
[45] Date of Patent: Jul. 20, 1999

[54] IRON DETECTING SENSORS

[75] Inventors: Marian L. Kruzel; Kurt S. Myers, both of Houston, Tex.

[73] Assignee: Ferro Sensor, Inc., Houston, Tex.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/645,255

[22] Filed: May 13, 1996

Related U.S. Application Data

[63] Continuation-in-part of application No. 08/512,950, Aug. 9, 1995, Pat. No. 5,516,697, which is a continuation of application No. 08/112,714, Aug. 26, 1993, abandoned.

[51] Int. Cl.[6] .................................................. G01N 33/20
[52] U.S. Cl. ............................. 422/56; 436/74; 436/84; 436/163; 436/169; 422/57; 422/58; 422/61
[58] Field of Search ............................. 436/74, 84, 163, 436/169; 422/56, 57, 58, 61

[56] References Cited

U.S. PATENT DOCUMENTS

| | | | |
|---|---|---|---|
| 3,836,331 | 9/1974 | Stookey | 436/84 |
| 4,224,034 | 9/1980 | Denney et al. | 436/84 |
| 4,308,027 | 12/1981 | Ceriotti | 23/230 B |
| 4,588,695 | 5/1986 | Takano et al. | 436/87 |
| 4,789,525 | 12/1988 | Warren, III et al. | 436/84 |
| 5,017,498 | 5/1991 | Fossati et al. | 436/84 |
| 5,039,618 | 8/1991 | Stone | 436/77 |
| 5,186,894 | 2/1993 | Katsuyama | 422/56 |
| 5,211,914 | 5/1993 | Vogel et al. | 422/56 |
| 5,223,436 | 6/1993 | Freitag et al. | 436/97 |
| 5,227,310 | 7/1993 | Sakamoto et al. | 436/169 |
| 5,244,631 | 9/1993 | Morikawa | 422/56 |
| 5,278,075 | 1/1994 | Stone | 436/73 |
| 5,364,792 | 11/1994 | Stone | 436/84 |
| 5,504,013 | 4/1996 | Senior | 436/165 |
| 5,516,697 | 5/1996 | Kruzel | 436/84 |
| 5,550,061 | 8/1996 | Stone | 436/84 |
| 5,763,281 | 6/1998 | Weisheit et al. | 436/74 |

OTHER PUBLICATIONS

*Annals New York Academy of Sciences* 102, Leland C. Clark, Jr. and Champ Lyons, "Electrode Systems for Continuous Monitoring in Cardiovascular Surgery", pp. 29 to 45, (1962).

*Biosensors: Fundamentals, Technologies and Applications*, Edited by F. Scheller and R.d. Schmid, "Biosensors for the Detection of Heavy Metal Ions and Fecal Matter", pp. 129 to 132, (1991).

*Biosensor Technology*, edited by Richard P. Buch et al., Chapter 2 "Solid State Potentiometric Sensors", pp. 17 to 38, (1990).

*Biosensors A Practical Approach*, edited by A.E.G. Cass, "Unmediated amperometric enzyme electrodes", pp. 1 to 17, (1990).

*Biosensors*, Elizabeth A.H. Hall, Chapter 1 "Biosensors in Context", pp. 1 to 29, (1991).

*Symposium: Hypertransfusion and iron chelation in thalassaemia*, edited by Askey/Birdwood, "The present state of iron–chelation therapy", Heinrick H. Peter, pp. 69–81, (Jun. 1984).

"Microbial Iron Compounds", J.B.Neilands, *Ann. Rev. Biochem.*, (1981), 50:715–31.

"Iron transport and storage", crichton and Charloteaux–Wauters, *Eur. J. Biochem.*, 164, 485–506, (1987).

*Concise Encyclopedia Biochemistry*, Second Edition, pp. 311–312, (1988).

Primary Examiner—Jill Warden
Assistant Examiner—Sharidan Carrillo
Attorney, Agent, or Firm—Kurt S. Myers

[57] ABSTRACT

The present invention is directed to iron sensors. Immobilized in close proximity of the potential or pH measuring surface of a proton sensing device, minute quantities of an iron chelator such as siderophores or transferring cause detectable variation of the potential or pH upon the binding of iron. The sensing devices for measuring this change in potential or pH include the iron chelator-modified ion-selective field effect transistors (IC-ISFET) and/or pH indicator papers of the present invention.

5 Claims, 3 Drawing Sheets

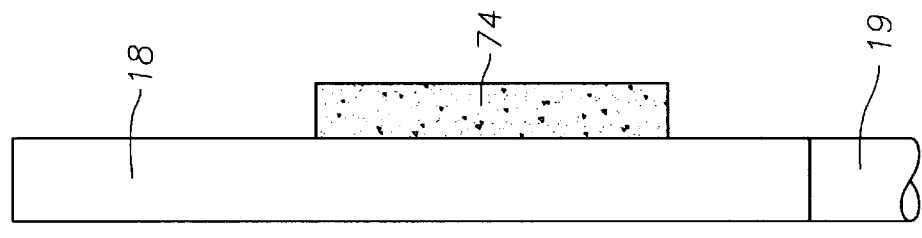
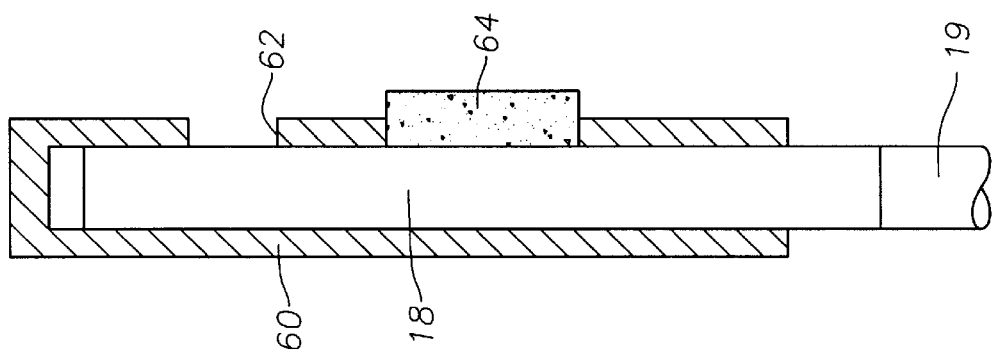
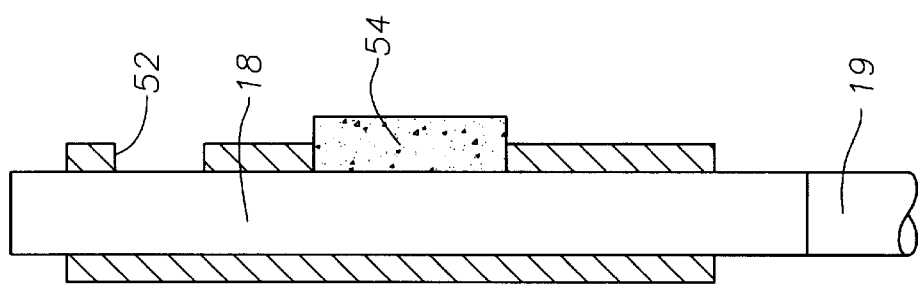

IRON DETECTING SENSORS

RELATED APPLICATIONS

This application is a continuation-in-part application of Ser. No. 08/512,950, filed Aug. 9, 1995 entitled "Biosensor For Detecting Iron", now U.S. Pat. No. 5,516,697, which in turn is a continuation application of Ser. No. 8/112,714, filed Aug. 26, 1993, also entitled "Biosensor For Detecting Iron", now abandoned.

FIELD OF THE INVENTION

The present invention is directed to iron sensors which use iron chelators such as siderophores or transferrins for detecting iron in a sample. The iron chelators release protons upon binding the iron, causing the change in potential or pH that is measured by a proton sensing device.

SUMMARY OF THE INVENTION

The present invention is directed to iron sensors. Immobilized in close proximity of the potential or pH measuring surface of a proton sensing device, minute quantities of an iron chelator such as siderophores or transferrin cause detectable variation of the potential or pH upon the binding of iron. The sensing devices for measuring this change in potential or pH include the iron chelator-modified ion-selective field effect transistors (IC-ISFET) and/or pH indicator papers of the present invention.

BACKGROUND OF THE INVENTION

Detection of bioaccessible iron is one of the most important measurements that can detect iron deficiency, iron overload or different types of immunological disorders.

To date iron is measured through a combination of blood tests that detect iron and iron binding capacity of transferrin, the protein that transports iron through the body. The current technology involves very sophisticated instrumentation which make this analysis prohibitively expensive and often requires qualified personnel to analyze the sample. Therefore, there is a need for the direct assay of iron that combines simplicity and economics. The present invention is directed to biosensors using iron chelators such as siderophores and transferrins for detecting the amount of iron in a sample.

Although the technology relating to biosensors has been developing over the last 30 years, the specific application of iron chelators for the detection of iron has not been disclosed. Various biocomponents (e.g. carbohydrates, amino acids, alcohols and certain proteins) are detected today with specifically designed potentiometric and amperometric electrodes. The original work on such electrodes was done by Clark Jr., L. C. and Lyons, C. published in *Ann. N.Y. Acad. Sci.* 102, p.29 (1962). In this first enzyme electrode, a glucose oxidase membrane was placed next to a platinum electrode to detect the products of the enzyme reaction in the presence of a substrate, glucose.

The characteristics of such electrodes are governed by the biorecognition of the analyte and the transport processes. In a recent edition of *Biosensors: Fundamentals, Technologies and Applications*, Edited by F. Scheller and R. D. Schmid, pp 129–132 (1991), a paper, "Biosensors for the Detection of Heavy Metal Ions and Fecal Contamination", discloses the use of phytochelatins, metallothioneins and polymerized glutathiones to complex and detect heavy metals. These materials however are not specific to iron or any other single heavy metal. In order to transduce the signal the authors, F.Binder et al, use a proton-sensitive field-effect transistor, generally referred to as an ion-selective field effect transistor (ISFET).

The ion-selective field effect transistor has been in development for many years. A chapter of the book *Biosensor Technolonogy*, edited by Buck et al. and published by Marcel Decker,Inc., 1990, entitled "Solid State Potentiometric Sensors" by Jiri Janata, pp 17–34, reviews the development of such ISFET sensors. The specific work describes a sensor that incorporates the principle of the enzymatic reactions that result in the production of protons.

In an article "Unmediated amperometric enzyme electrodes" by George Wilson and Daniel Thevenot published in *Biosensors, A Practical Approach Series*, (edited by A. E. G. Cass and published by Oxford University Press), 1990, pp 1–17, discloses some techniques in producing electrodes. These electrodes are used in reactions which produce a small molecular weight electroactive species. Since these sensors can be used to monitor such a reaction without the need of a mediator, the sensor is called a "unmediated amperometric enzyme electrode".

A key development in later electrodes was the employment of membrane technology in order to eliminate the interference by substances other than the analyte electroactive substance. An excellent overview of biosensors in this regard, their development and application, is presented in *Biosensors*, edited by A. H. Hall and published by Prentice Hall, 1991.

BRIEF DESCRIPTION OF THE DRAWINGS

FIG. 5 is a side view of a skirt on pH sensitive paper on a stick, the partial cross-section illustrating the skirt, to modify pH paper according to the present invention;

FIG. 6 is a side view of a cap over pH sensitive paper on a stick, the partial cross-section illustrating the cap, to modify pH paper according to the present invention; and FIG. 7 is a side view of pH sensitive paper on a stick modified by a layer of an iron chelator to provide an iron sensor according to the present invention.

DESCRIPTION OF THE PREFERRED EMBODIMENTS

The sensors of the present invention provide a simple device for giving a predictive iron level in various kinds of samples. In the sensors of the present invention iron chelators, preferably siderophores or transferring, are used to sequester iron from a sample with the accompanied release of protons of hydrogen ($H^+$) and the change of potential or pH is measured when the iron is sequestered by the iron chelator. The sensing devices for measuring this change in potential or pH include the iron chelator-modified ion-selective field effect transistors (IC-ISFET) and/or pH indicator papers of the present invention. The unique feature of the present invention is that the iron chelator is maintained or immobilized in close proximity with the potential or pH measuring element to give a reagentless sensing system that is selective or specific to a target analyte, iron.

The basic method and apparatus is described in detail in Ser. No. 08/512,950, entitled "Biosensor For Detecting Iron", now U.S. Pat. No. 5,516,697, which is incorporated herein by reference.

As disclosed in the patent, transferrins bind two atoms of iron with binding constants from $10^{25}$ up to $10^{30}$ M$^{-1}$ (mole) depending upon specific conditions. Such a high affinity to iron makes this family of proteins an extremely good material for the quantitative assay of iron. Another family of compounds having even greater binding constants to iron are the siderophores. Suitable siderophores for use in the present invention are the catecholamides, ferrioxamines, fusarinines and coprogens. Specific siderophores are enterobactin and agrobactin/parabactin (binding constant about $10^{32}$ M$^{-1}$), Desferrioxamine E (binding constant about $10^{32}$ M$^{-1}$) and rhodetorulic acid (binding constant about $10^{31}$ M$^{-1}$), Table III in paper "The present state of iron-chelation therapy", by Heinrich H. Peter, Symposium "Hypertransfusion and iron chelation in thalassaemia", editors M.Aksov/A. F. B.Birdwood, Jun. 1984, pp 69–81. Desferrioxamine-B is a commercially available siderophore compound produced by Ciba-Geigy which may be used as the iron chelator of the iron sensors of the present invention and is now the preferred iron chelator.

Figure 1:
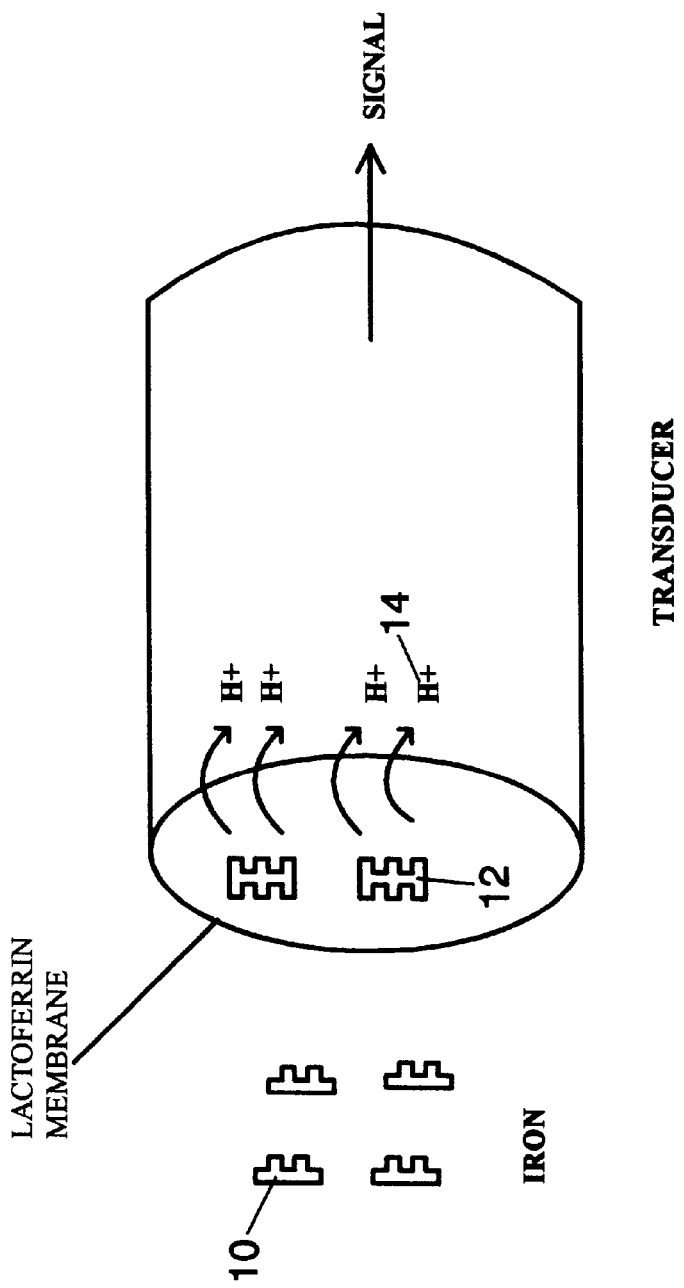
FIG. 1 is a schematic drawing illustrating the concept of the present invention showing the sequestering of iron from a sample, the release of protons and the change in the potential in a sample due to the release of protons.

FIG. 1 is used to illustrate the general reaction in a schematic manner between an iron chelator and the iron in a sample. The specific construction of the iron sensors of the present invention will be set forth hereinafter. A sample containing iron is contacted with an iron chelator-modified ion-selective field effect transistors (IC-ISFET) and/or pH indicator papers of the present invention. The iron 10 is sequestered from the sample by the iron chelator 12. A fixed number of protons 14 are released which are directly proportional to the atoms of iron sequestered. The change of potential or pH, caused by the released protons in the solution, is measured.

There are several alternatives in producing an iron chelator-modified ISFET as an iron sensor. As will be described in more detail hereinafter, the alternatives are in the means or structure used to maintain or immobilize the iron chelator in the immediate or close proximity of the potential sensing elements; namely, the chip which measures the concentration of hydrogen ions and the reference electrode of an ion-selective field effect transistor (ISFET).

Figure 2:
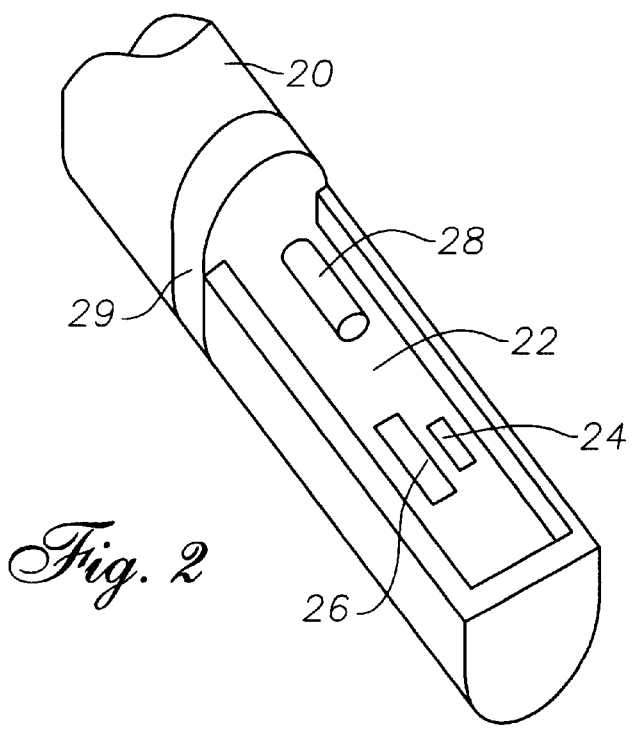
FIG. 2 is an isometric view of the end of a probe of an ion-sensitive field effect transistor (ISFET) device.

Referring now to FIG. 2, the end of a probe 20 has a hollowed out portion 22. In the hollowed out portion 22 of probe 20 is a chip 24 and a reference electrode 26 which are the sensing elements of an ion-selective field effect transistor (ISFET). The chip 24 and reference electrode 26 have the electrical connections within the probe 20 connected to the software circuitry and display box (not shown). The probe 20 also has a temperature sensing element 28 also connected to the circuitry. A suitable probe for the iron sensors of the present invention is the probe manufactured for Sentron Incorporation's Sentron 2001 pH meter. The probe fits into the smallest standard test tube. Other probes which are modifiable are the probes of the Corning 360i pH system, manufactured by Corning Incorporated, Corning N.Y.; or the Orion 610 pH system, manufactured by Orion Analytical Technology, Inc., Boston, Mass.

Figure 3:
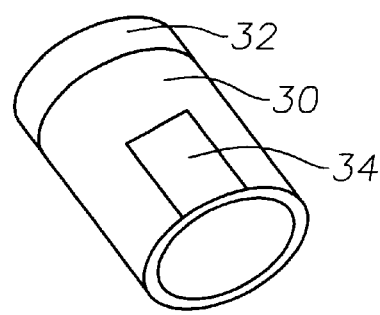
FIG. 3 is an isometric view of one embodiment, a skirt to cover the probe of FIG. 2, to modify the ISFET according to the present invention.

One alternative for modifying the probe 20 as a iron sensor is illustrated in FIG. 3. In this embodiment, a skirt 30 is pulled over the end of probe 20. The skirt 30 may have an elastic band 32 to fit over the waist 29 of the probe 20. An iron chelator is immobilized on a rectangular portion 34 of the skirt 30.

The skirt 30 is manufactured as a continuous strip. A suitable material for making the skirt 30 is a cellulose acetate membrane or a nylon membrane. The rectangular portion 34 containing the iron chelator may be a treated portion of the skirt material or a separately prepared strip of a membrane, which is then cut and bonded to the skirt material.

The preparation of the rectangular portion 34 is illustrated in the following examples:

EXAMPLE 1

In this example Desferrioxamine-B is covalently immobilized on the surface of a cellulose acetate membrane.

A mixture of 24 g cyclohexanone, 24 g of acetone and 1 g of cellulose acetate (39.8% acetyl content, available from Aldrich Chemical Company) is stirred at room temperature for 1 hour. The resulting solution is spread over a clean and dry glass plate and the solvent is evaporated in 1 hour. The membrane is removed from the glass by immersing the plate in distilled water and then is cut for small pieces (2 cm square). Four to five pieces of membrane are suspended in 100 ml of 0.1 M sodium periodate for 20 minutes at room temperature. The membranes are washed with distilled water and then soaked with 10 ml of 10 mg/ml solution of bovine serum albumin (BSA) in 0.1 M borate buffer, pH 9.0, for 2 hours. An aliquot of 9 ml of BSA solution is removed from the membranes and 4 mg of sodium cyanoborohydride is added to the remaining 1 ml of BSA. The mixture is incubated for 2 hours at room temperature and then washed with distilled water. The BSA-cellulose acetate membranes are suspended in 2 ml of a p-benzoquinone activated Desferrioxamine-B (prepared from 100 ul of p-benzoquinone and 500 ul of a 20 mg/ml solution of Desferrioxamine-B, followed by the removal of excess p-benzoquinone by gel filtration through Sephadex G-25), pH 8.2 for at least 24 hours at room temperature. The membranes are removed from the mixture and washed extensively with 0.15 M sodium chloride. The membranes are then used in the skirt 30 as described hereinabove to cover an ISFET probe.

EXAMPLE 2

In this example Desferrioxamine-B is covalently immobilized to the surface of a nylon membrane.

A ten centimeter square of nylon immunoaffinity membrane (Biodyne, a product and trademark of Pall Incorporated, Glen Cove, N.Y. which is 120 um thick and has a 0.2 um pore diameter or a nylon-66 product having a 0.2 um pore diameter of Schleicher & Schuell, Inc., Keene, N.H.) is immersed in 10 ml of a 1.5 mg/ml solution of Desferrioxamine-B in 0.1 M phosphate buffer, pH 7.4, at 40° C. for 24 hours. The saturated membrane is then washed three times with 10 ml of 1M sodium chloride in 0.1 M sodium phosphate buffer, pH 7.4. The membrane is then used as set forth hereinabove.

From the examples hereinabove, it is clear that the various siderophores may be immobilized on a membrane material and are then suitable to be used to modify a ISFET probe to produce an iron sensor of the present invention. The significant requirement of the modification to the ISFET probe is that the iron chelator must be maintained in close proximity to the potential sensing elements of the ISFET device.

When drops of sample are used to determine the qualitative or quantitative amounts of iron in a sample, the probe structure itself can maintain the iron chelators in close proximity. Referring again to FIG. 2, the hollow portion 22 of probe 20 can maintain the sample and iron chelator in this portion of the probe 20 to measure the protons released when the iron is bound to the chelator with the release of protons.

The method for obtaining a predictive iron level in a sample is illustrated by using only the probe 20 with the hollow portion 22. A drop of a specific siderophore such as Desferrioxamine-B is applied over the chip 24 and the reference electrode 26 and the potential measured, a direct relation to the concentration of hydrogen ions or pH of the siderophore. This measured potential is stored in the software of the recording device. The probe is then cleaned before adding a drop of sample containing iron. In building the algorithm to give the predictive iron level in an unknown sample, the drop of sample contains a known concentration of iron and the potential or pH is measured. Then a drop of siderophore is added to the sample and the potential or pH of the combined drops is measured. This is compared to a calculated potential, calculated by the software, based on the known amount of sample having a known potential and on the known amount of siderophore having a known potential. The difference is caused by the released protons when the siderophore binds the iron with the release of hydrogen ions. The same procedure, namely adding a drop of sample then a drop of siderophore, is then used on a sample with an unknown amount of iron and the measured potential is compared to the algorithm to determine the concentration.

The method for obtaining a predictive iron level in a sample is illustrated when using the skirt 30 with the probe 20. The probe 20 is inserted into a sample containing iron and the potential is measured. The skirt 30 is then placed on the probe 20 so that the elastic band 32 is around the waist 29 of the probe 20 and the iron chelator treated portion 34 is over the sensing elements, the chip 24 and reference electrode 26. The probe 20 is then again inserted into the sample and the potential measured.

Figure 4:
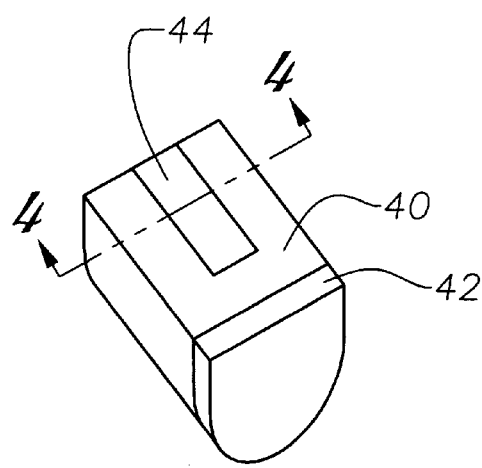
FIG. 4 is an isometric view of another embodiment, a tip or thimble to cover the probe of FIG. 2, to modify the ISFET according to the present invention.
Figure 4A:
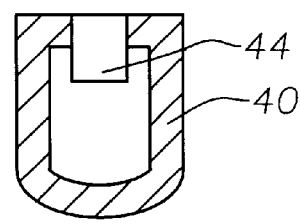
FIG. 4a is a cross section along 4—4 of FIG. 4.

Referring now to FIG. 4, another alternative to modify the ISFET probe 20, is a cap or thimble 40. The closed end of cap 40 may be an elastic material 42. An iron chelator treated rectangular portion 44 is part of the cap material or may be below the cap material as shown in FIG. 4A. The iron chelator membranes of Examples 1 or 2 are suitable membranes for the rectangular portion 44 of this embodiment. This embodiment of the cap 40 illustrates another way in which the iron chelator is immobilized in close proximity to the sensing elements of the ISFET.

Likewise, there are several alternatives in producing an iron chelator-modified pH paper as an iron sensor. As will be described in more detail hereinafter, the alternatives are in the means or structure used to maintain or immobilize the iron chelator in the immediate or close proximity of the pH paper.

One alternative for modifying a pH sensitive paper 18 as an iron sensor is illustrated in FIG. 5. In this embodiment, a skirt 50 is pulled over the end of paper 18 which is on a stick 19 made of wood or plastic. The skirt 50 has a window 52 to provide direct access to the sample. An iron chelator is immobilized on a rectangular portion 54 of the skirt 50

The skirt 50 is made is the same manner as illustrated in Example 1 or 2 except that the size and shape is such to fit a pH paper stick 19.

Another alternative for modifying pH sensitive paper 18 as an iron sensor is illustrated in FIG. 6. In this embodiment, a cap or thimble 60 is pulled over the end of paper 18 which is on a stick 19 made of wood or plastic. The cap 60 has a window 62 to provide direct access to the sample. An iron chelator is immobilized on a rectangular portion 64 of the cap 60.

The cap 60 is made is the same manner as illustrated in Example 1 or 2 except that the size and shape is such to fit a pH paper stick 19.

Still another alternative for modifying pH sensitive paper 18 as an iron sensor is illustrated in FIG. 7. In this embodiment, an iron chelator is immobilized on a rectangular portion 74 of the paper 18 on stick 19.

EXAMPLE 3

In this example Desferrioxamine-B is immobilized to the surface of pH paper on a plastic strip by reticulation with glutaraldehyde.

About 10 mg of Desferrioxamine-B and 10 mg of bovine serum albumin are dissolved in 1 ml of distilled water. The resulting solution is applied over the surface of the pH sensitive paper on a plastic strip. The protein solution is allowed to dry for about 2 hours so that the solution forms a membrane on the surface. About 100 ul of 10% (v/v) glutarahyde in 0.05 M sodium phosphate buffer (pH 7.0) is applied over the protein layer and incubated for about 1 hour at room temperature. The incubated membrane is then washed with the same sodium phosphate buffer and allowed to dry at room temperature for about 2 hours. The strip with immobilized Desferrioxamine-B covers a known pH sensitive paper (e.g. Fisher Scientific Company, Catalog No. 14-853-93, 14-853-100 or 14-853-79). The strips are stored in a dry cool place protected from the direct exposure to light.

With the color sensitive pH papers, the measurement of iron is determined from comparing the measured pH of a sample containing iron and a chosen iron chelator (chemically reacted) with the calculated pH of the sample containing iron and the pH of the chosen iron chelator. This calculation in building the algorithm to give the predictive iron level is done by using a drop of known concentration of sample and a drop of chosen iron chelator and plotting the pH of the combined materials (no chemical reaction). This calculated pH will form a chart for each iron chelator used and each variance of pH of the sample over a range of pH. In making the algorithm, a separate stick of pH paper may be used for each of the sample, chosen iron chelator and the combined sample and iron chelator or alternatively, three separate portions or spots on the same pH paper or stick may be used. This will depend on the instrumentaion used to compare the colors on the pH paper. This should also explain that once the algorithm of a specific, chosen iron chelator is available, the pH paper sticks for an unknown sample need only a measurement of the pH of the sample and the combined sample and chosen iron chelator to make the predictive determination of iron in the sample.

Still other alternatives of modifying systems which are conventionally used to measure pH are possible according to the present invention. For example, instead of modifying the ISFET device or the pH sensitive paper, the sample may be modified and the usual potential or pH sensors can be used. In this embodiment, the preferred material is an iron chelator-modified glass bead. A known amount of iron chelator is applied to each bead and thus, the addition of a known number of beads to a known volume of sample containing iron will provide a potential or pH which is measured to determine a predictive level of iron in the sample. The following example illustrates the coating of beads with an iron chelator.

EXAMPLE 4

In this example Desferrioxamine-B is immobilized on a control pore glass (CPG).

A mixture of 1 ml of animopropyl substituted CPG beads (mean-pore diameter 200 nm, 80–120 mesh, obtained from Corning Glass) with 10 ml of glutaraldehyde (2.5% in 0.1 M sodium phosphate buffer, pH 7.0) is shaken gently for about 1 hour. The material is washed with two 10 ml aliquots of distilled water and two aliquots of the 0.1 M sodium phosphate buffer, pH 7.0. 200 mg of Desferrioxamine-B is added to the 4 ml of the same sodium phosphate buffer, which is then added to the CPG suspension and shaken gently at 4° C. for about 12 hours. The resulting preparation is washed twice with 10 ml aliquots of the sodium phosphate buffer, and the washed material is then shaken with 4 ml of 2 mM glycine in the sodium phosphate buffer, followed again by two washings with 10 ml aliquots of the sodium phosphate buffer. The resulting preparation is then washed with two 5 ml aliquots of 0.5 M sodium chloride in 0.1 M sodium phosphate buffer, pH 7.0, followed by two washings with 10 ml aliquots of 20 mM Tris/HCl buffer, pH 7.4.

The Desferrioxamine-B-modified CPG beads are placed in 20 mM Tris/HCl buffer, pH 7.4, for 2 hours before use.

There are a large number of applications for identifying iron or a change in concentration of iron in specific samples. For example, contaminated solid samples, such as meat or earth, liquid samples, such as contaminated water from streams or rivers, and gas samples, such as air samples, are all able to be monitored by the Desferrioxamine-B-modified CPG beads in a cartridge or a fixed volume container.

The sensors of the present invention has many more uses than the measurement of iron as a diagnostic tool for mammals. The importance of a diagnostic tool is by no means minimized since the sensor is an important tool having preventive and therapeutic applications. Other applications for the sensor of the present invention are to test for spoilage or contamination especially of meat, water, soil and gases. The presence of dispersed solids also may be part of the samples measured for iron by the biosensors of the present invention.

We claim:

1. A pH paper for measuring iron in a sainpic comprising:
    a pH paper color sensitive to protons mounted on a support; and
    an iron chellator-modified membrane adjacent to a portion of said pH paper that contacts said sample, said iron chelator-modified membrane containing an iron chelator selected from the group consisting of siderophores and transferrins, wherein said chelator sequesters iron from the sample and releases protons which results in a color change of said pH paper.

2. The pH paper according to claim 1 wherein said iron chelator-modified membrane is a sidcrophore is a siderophore selected from the group consisting of catecholamides, ferrioxamines, fusarinines and coprogens.

3. The pH paper according to claim 1 wherein said support is a stick.

4. The pH paper according to claim 3 wherein said iron chelator-modified membrane is formed in the shape of a skirt which is pulled over an end of said stick.

5. The pH paper according to claim 3 wherein said iron chelator-modified membrane is shaped in the form of a cap positioned at an end of said stick.

* * * * *